(12) United States Patent
Toth (10) Patent No.: US 12,121,645 B2
(45) Date of Patent: *Oct. 22, 2024

(54) METHOD AND SYSTEM FOR REMOVING EXUDATES FROM A WOUND SITE

(71) Applicant: CONVATEC TECHNOLOGIES INC., Las Vegas, NV (US)

(72) Inventor: Landy Aaron Toth, Newton, PA (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 1080 days.

This patent is subject to a terminal disclaimer.

(21) Appl. No.: 16/995,001

(22) Filed: Aug. 17, 2020

(65) Prior Publication Data
US 2020/0376177 A1    Dec. 3, 2020

Related U.S. Application Data

(63) Continuation of application No. 13/992,623, filed as application No. PCT/US2011/063686 on Dec. 7, 2011, now Pat. No. 10,780,200.

(60) Provisional application No. 61/421,012, filed on Dec. 8, 2010, provisional application No. 61/421,006, filed on Dec. 8, 2010.

(51) Int. Cl.
*A61M 1/00*   (2006.01)
*A61M 27/00*   (2006.01)

(52) U.S. Cl.
CPC ............. *A61M 1/74* (2021.05); *A61M 1/68* (2021.05); *A61M 1/78* (2021.05); *A61M 1/82* (2021.05); *A61M 1/96* (2021.05); *A61M 1/962* (2021.05); *A61M 1/982* (2021.05); *A61M 1/67* (2021.05); *A61M 1/80* (2021.05); *A61M 27/00* (2013.01); *A61M 2205/075* (2013.01); *A61M 2205/8206* (2013.01); *A61M 2209/088* (2013.01)

(58) Field of Classification Search
CPC .............. A61M 1/0011; A61M 1/0023; A61M 1/0066; A61M 1/0072; A61M 27/00; A61M 1/0009; A61M 1/82; A61M 2205/075; A61M 2205/8206; A61M 2205/088
USPC ........................................................ 604/321
See application file for complete search history.

(56) References Cited

U.S. PATENT DOCUMENTS

| | | | |
|---|---|---|---|
| 4,850,955 A * | 7/1989 | Newkirk | A61M 27/002 604/9 |
| 10,016,537 B2 | 7/2018 | Menon et al. | |

(Continued)

FOREIGN PATENT DOCUMENTS

| | | |
|---|---|---|
| EP | 3187204 A1 | 7/2017 |
| EP | 3556407 A1 | 10/2019 |

(Continued)

*Primary Examiner* — Andrew J Mensh
(74) *Attorney, Agent, or Firm* — TAFT STETTINIUS & HOLLISTER LLP; Ryan O. White; Derek B. Lavender (57) ABSTRACT

An apparatus (10) for controlling flow of fluid from a wound site of a patient including a cavity (28) connectable to a wound site and a reservoir (16). The cavity (28) may have a first deformed state, and a second state in which it is not deformed or less deformed than in the first state. The cavity (28) may be adapted to manage fluid flow between the wound site and the reservoir (16) during transition of the cavity (28) between the first state and the second state. An actuator element (64) of the apparatus (10) may be adapted to operate on the chamber (28) to transition the cavity (28) from the second state to the first state.

20 Claims, 6 Drawing Sheets

(56) References Cited

U.S. PATENT DOCUMENTS

| | | | |
|---|---|---|---|
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |

(56) References Cited

U.S. PATENT DOCUMENTS

| | | |
|---|---|---|
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 11,400,204 B2 | 8/2022 | Coulthard et al. |
| 11,813,058 B2 | 11/2023 | Shuler |
| 2002/0013545 A1* | 1/2002 | Soltanpour ......... A61F 9/00781 604/9 |
| 2006/0155260 A1 | 7/2006 | Blott et al. |
| 2006/0172000 A1 | 8/2006 | Cullen et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2008/0108977 A1* | 5/2008 | Heaton ................ A61M 1/98 604/355 |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2011/0288511 A1* | 11/2011 | Locke ..................... A61M 1/60 604/319 |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |

(56) References Cited

U.S. PATENT DOCUMENTS

| | | |
|---|---|---|
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | MacPhee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | MacPhee et al. |
| 2019/0388589 A1 | 12/2019 | MacPhee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powe |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |

(56) References Cited

U.S. PATENT DOCUMENTS

| | | |
|---|---|---|
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaeckiein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246190 A1 | 8/2020 | Luckemeyer et al. |
| 2020/0246191 A1 | 8/2020 | Lu et al. |
| 2020/0246194 A1 | 8/2020 | Gonzalez et al. |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0253788 A1 | 8/2020 | Rehbein et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0269028 A1 | 8/2020 | Hegg |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289326 A1 | 9/2020 | Nielsen et al. |
| 2020/0289327 A1 | 9/2020 | Hansen et al. |
| 2020/0289328 A1 | 9/2020 | Luckemeyer et al. |
| 2020/0289346 A1 | 9/2020 | Hansen et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306092 A1 | 10/2020 | Rehbein et al. |
| 2020/0306094 A1 | 10/2020 | Kushnir et al. |
| 2020/0306426 A1 | 10/2020 | Rice et al. |
| 2020/0306428 A1 | 10/2020 | Ingram et al. |
| 2020/0306430 A1 | 10/2020 | Rehbein et al. |
| 2020/0315853 A1 | 10/2020 | Waite |
| 2020/0315854 A1 | 10/2020 | Simmons et al. |
| 2020/0315894 A1 | 10/2020 | Churilla et al. |
| 2020/0316271 A1 | 10/2020 | Lin |
| 2020/0316272 A1 | 10/2020 | Simpson |
| 2020/0316273 A1 | 10/2020 | Hegg |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |

FOREIGN PATENT DOCUMENTS

| | | |
|---|---|---|
| EP | 3569260 A1 | 11/2019 |
| EP | 3622975 A1 | 3/2020 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| EP | 3669898 A1 | 6/2020 |
| EP | 3669899 A1 | 6/2020 |
| EP | 3409304 B1 | 7/2022 |
| EP | 2311509 B2 | 8/2022 |
| EP | 2902068 B2 | 9/2022 |
| EP | 3248623 B1 | 8/2023 |
| GB | 2579211 A | 6/2020 |
| GB | 2579368 A | 6/2020 |
| WO | 2005018543 A2 | 3/2005 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |

(56) References Cited

FOREIGN PATENT DOCUMENTS

| | | |
|---|---|---|
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |
| WO | 2020144347 A1 | 7/2020 |
| WO | 2020150548 A1 | 7/2020 |
| WO | 2020159675 A1 | 8/2020 |
| WO | 2020159677 A1 | 8/2020 |
| WO | 2020159678 A1 | 8/2020 |
| WO | 2020159823 A1 | 8/2020 |
| WO | 2020159859 A1 | 8/2020 |
| WO | 2020159892 A1 | 8/2020 |
| WO | 2020161086 A1 | 8/2020 |
| WO | 2020197759 A1 | 10/2020 |
| WO | 2020197760 A1 | 10/2020 |
| WO | 2020198484 A1 | 10/2020 |
| WO | 2020201879 A1 | 10/2020 |
| WO | 2020213998 A1 | 10/2020 |

\* cited by examiner

METHOD AND SYSTEM FOR REMOVING EXUDATES FROM A WOUND SITE

CROSS-REFERENCE TO RELATED APPLICATIONS

This application is a continuation of U.S. patent application Ser. No. 13/992,623, having the title "Method and System for Removing Exudates from a Wound Site", filed Jul. 26, 2013, which is a U.S. National Phase of International Application No. PCT/US2011/63686, filed on Dec. 7, 2011, that claims benefit of the filing date of U.S. Provisional Patent Application No. 61/421,012, filed Dec. 8, 2010, entitled "Method and System for Removing Exudates from a Wound Site", and U.S. Provisional Patent Application No. 61/421,006, filed Dec. 8, 2010, entitled "System and Method for Applying Oscillating Pressure to a Wound Site", the disclosures of which are hereby incorporated herein by reference.

BACKGROUND OF THE INVENTION

Typical systems for removing exudates from a wound site can be bulky, low capacity and/or passive. As a result, the systems cannot be readily portable or provide satisfactory exudate management. Also, typical systems can be prone to leak failures, thus rendering them less useful for use on even moderately sized wounds. Further, typical systems having an air-based pump can be too large, expensive and inefficient to be usable in wearable applications.

For example, a typical bulky system for removing exudates uses air-based accumulators that move a lot of air to sustain a vacuum, and has a large container with a gravity trap for exudates, which increases the size of the system independent of the amount of exudate being removed. Such systems typically can introduce leaks into the fluid flow lines of the system, and also overcompensate on power capability to ensure a vacuum is maintained in the presence of a substantial leak. Further, such systems usually are designed to handle the largest expected wounds, and to have a large configuration.

Typical low capacity systems for removing exudates, although being more portable, have very small containment systems. Such smaller containment systems often may not be sufficiently large enough to hold the volume of exudates liberated daily from moderately or highly exuding wounds. In many cases, the containment systems cannot hold more fluid than a moist wound dressing.

Further, typical passive systems for removing exudates, which have spring-loaded canisters and apply a vacuum until the canisters become full or until a leak forms at a dressing, can be very leak prone, such as at connectors, around dressing seals, etc. Also, typical passive systems cannot apply a vacuum intermittently. The passive systems further can include disposable canisters, such that they are not environmentally friendly.

Therefore, there exists a need for a system for removing exudates from a wound site which is portable, may be manufactured under less demanding component tolerances, may be of relatively small size, may sustain therapy in the event of a leak, may provide effective intermittent vacuum therapies and may provide therapy for larger wounds.

BRIEF SUMMARY OF THE INVENTION

In accordance with an aspect of the invention, an apparatus for controlling flow of fluid from a wound site of a patient may include a chamber connectable in fluid communication with the wound site and a reservoir for receiving and holding fluid. The chamber may have a first state, in which the chamber is deformed, and a second state, in which the chamber is not deformed or less deformed than in the first state. The chamber may be adapted to manage fluid flow between the wound site and the reservoir during transition of the chamber between the first state and the second state. In addition, the apparatus may include an actuator element adapted to operate on the chamber to transition the chamber from the second state to the first state.

In accordance with another aspect of the invention, an apparatus for controlling flow of fluid from a wound site of a patient may include a passive pump unit including a chamber having an input for receiving the fluid from the wound site of the patient conveyed over a conduit connectable in fluid communication with the input and an output for providing the received fluid from the chamber. The apparatus may further include an actuator element operable to create a pressure within the chamber for drawing the fluid from the wound site through the conduit and the input and into the chamber. The chamber may be adapted to hold the received fluid without the received fluid flowing through the input and the output, and to provide the received fluid from the chamber through the output without the received fluid flowing through the input.

In another embodiment of the present disclosure there is provided a vacuum wound therapy apparatus including a chamber having a first wall and a second wall and a cavity disposed within the chamber. The cavity is configured for fluid communication with a wound site and with a reservoir that receives and holds wound exudate. The cavity includes an input for communication with the wound site, an output for communication with the reservoir, and a first non-rigid, deformable wall in fluid communication with the chamber with the first non-rigid, deformable wall opposing at least one of the first wall and the second wall. The cavity includes a first state being deformed and a second state being non-deformed or less deformed than the first state, wherein the cavity is adapted to draw exudate from the wound site into the cavity and to manage exudate flow between the wound site and the reservoir during transition of the cavity between the first state and the second state. A piezoelectric device is located at the first wall and in contact with the cavity, wherein the piezoelectric device is adapted to deform the first non-rigid deformable wall of the cavity in the direction of the second wall to transition the cavity from the second state to the first state.

In a further embodiment of the present invention, there is provided a vacuum wound therapy apparatus including an active element having a wall defining a chamber and a pump having an outlet in fluid communication with the chamber. A cavity is disposed within the chamber and includes an input for communication with a wound site, an output for communication with a reservoir, and a non-rigid deformable wall in fluid communication with the chamber. A controller is operatively connected to the pump and includes a processor and a memory, configured to store instructions. Thee processor is configured to execute the stored instructions to: actuate the pump to apply a fluid pressure within the chamber to transition the cavity from an expanded state to a compressed state to force exudate from the cavity to a reservoir.

DETAILED DESCRIPTION

Figure 1:
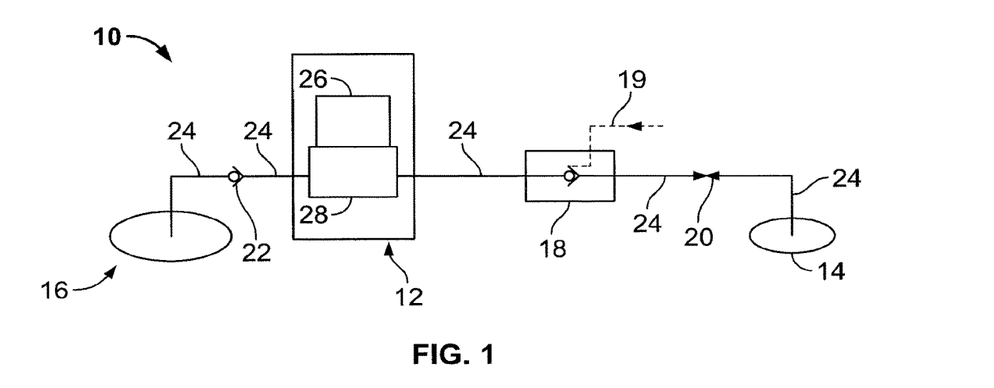
FIG. 1 is a block diagram of a system for removing exudates from around site, in accordance with an aspect of the invention.

FIG. 1 illustrates a system 10 for removing exudates from a wound site, in accordance with an aspect of the present invention. Referring to FIG. 1, the system 10 may include an apparatus 12 for controlling flow of fluid from a dressing 14 that may be applied to a wound site of a patient, a reservoir 16 for receiving and holding exudates and fluid from a wound site, a one-way inlet valve 18, a one-way outlet valve 22 and an optional closure device 20. The apparatus 12 may be connected, using conduits 24, to be in fluid communication with the wound site through the inlet valve 18 and the closure device 20, and to be in fluid communication with the reservoir 16 through the outlet valve 22.

In one embodiment, the reservoir 16 may be a collapsible chamber that slowly expands as it fills with exudates and fluid. In addition, the reservoir may be in the form of a bag, and may be adapted to couple to clips, bands or the like that may be used to fasten the bag-shaped reservoir to clothing, a patient's appendage or a bedside table, etc., during use. In another embodiment, the reservoir may include a filter for gas liberation, and a charcoal filter to minimize odor.

In one embodiment, the conduits 24 may be tubes formed using film processes or by extrusion processes. For example, the conduit may be a flexible conduit adapted not to collapse during use. In addition, the conduits may include odor barriers to reduce smell during use of the inventive system. In another embodiment, the conduits may be flat, thermoformed channels.

In a further embodiment, one or more of the conduits may be formed from two flat strips of thin flexible material welded or bonded together along their long edges to form a channel. The channel may also contain one or more spacer strips welded or bonded to the walls of the channel to ensure a fluid path is maintained even when the channel is folded or crushed or subjected to a vacuum pressure. The advantage provided by this feature is that the channel is low profile and lightweight to assist with portability and discretion. See, for example, PCT/GB2006/002806 and PCT/GB2006/002097, incorporated by reference herein.

The outlet valve 22 may be arranged in the system 10 to permit fluid flow only in a direction from the apparatus 12 to the reservoir 16. The inlet valve 18 may be arranged in the system 10 to permit fluid flow only in a direction from the dressing 14 to the apparatus 12. The valves 18 and 22, which are inline to the flow to and from the apparatus 12, may seal upon application of back pressure, such as may occur during a process to purge material from within the apparatus 12 and cause the purged material to be conveyed to and into the reservoir 16. Exemplary valves may include flap valves, flappers, flanges, anti-reflux valves, ball valves, duck bill valves, etc.

In one embodiment, the valve 18 may include a pilot valve that automatically, when pressure in one direction closes the valve, does not allow flow, and when there is pressure in the opposite direction, immediately opens the valve and allows flow. In an alternative embodiment, the pilot valve 18 may remain positively closed in either direction, or open in a desired direction only upon application of a separate pilot signal 19. The pilot signal 19 may be an electrical signal, such as from a controller of the apparatus 12, to open the valve. Alternatively, the pilot signal may be based on fluid pressure increasing to a certain level through a pilot port, which then fully opens a main valve.

In another embodiment, the one-way valves 18 and 22 may be optimized to avoid their becoming obstructed by gels, proteins and solid masses in the fluids being communicated there through.

The closure device 20 may be a valve operable to prevent fluid flow in any direction therethrough, and also permit fluid flow therethrough in a single direction, such as from the dressing to the apparatus 12.

The apparatus 12 may include a pump element 26 associated with an inline, self-filling pump cavity or chamber 28. The pump element 26 may be an active or mechanically operated component which may operate to create a pressure or a vacuum in the pump cavity, so as to draw exudates from a wound site into the pump cavity and to force exudates being retained in the pump cavity from the pump cavity into a storage element, such as the reservoir 16.

Figure 2:
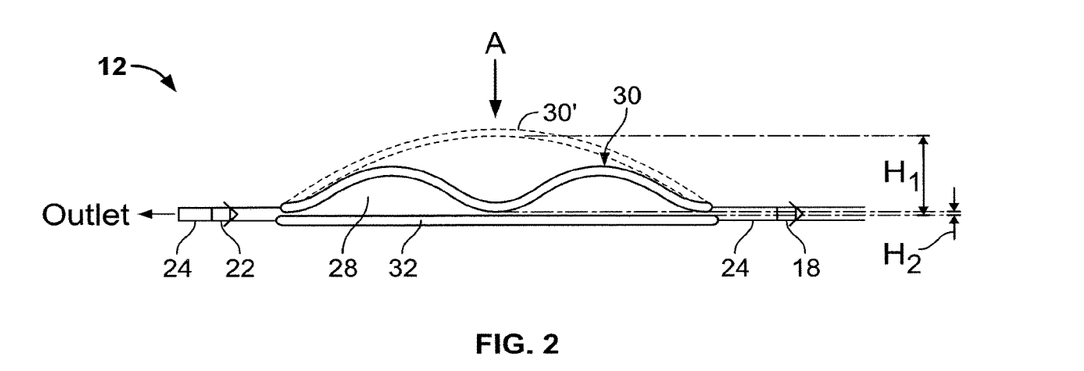
FIG. 2 is a schematic, cross-sectional view of an apparatus for controlling fluid flow from a wound site, in accordance with an aspect of the invention.

Referring to FIG. 2, in one embodiment the apparatus 12 may include a deformable top wall 30 opposing a rigid or substantially non-deformable back plate 32, which in combination form a self-filling cavity or chamber 28. The top wall 30 may recover its original shape after being deformed in the direction of the back plate, and include resilient material. The top wall 30, when in a non-deformed state as indicated by dashed lines 30' in FIG. 2, or a partially deformed state, may be acted upon to become deformed or further deformed to obtain a desired deformed state. The top wall 30 may be deformed, for example, by applying a force on the top wall 30 in a direction indicated by arrow A, toward the opposing base plate 32, to cause a portion of the top wall 30 to deform and move in the direction of the base plate 32. When the top wall 30 is deformed, a distance or height between a portion of the top wall 30 that is deformed and an opposing portion of the base plate 32 decreases, respectively, from a height H1 to a height H2 as shown in FIG. 2. The deformation of the top wall 30 reduces the space between the deformed portion of the top wall 30 and the base plate 32, thereby reducing the volume of the cavity 28 defined by the combination of the top wall and base plate. As the valve 18 in communication with the inlet of the cavity 28 prevents fluid flow from the apparatus 12 toward the dressing 14, when the top wall 30 is being deformed, contents, such as fluid or exudate from a wound site retained within the cavity, may be forced through the valve 22 and into the reservoir 16. The emptying of the contents from within the cavity may be part of a purging process performed at the apparatus 12.

When a force acting upon the top wall 30 is released after the top wall 30 is deformed by application of such force, such as shown in FIG. 2, the top wall 30 may begin to recover its original non-deformed shape during a recovery process, in which the deformed top wall is permitted to become less deformed and return to its non-deformed state. As the top wall 30 becomes less deformed and is transitioning from a deformed state to a less deformed state and ultimately its non-deformed state, the volume of the cavity 28 increases. During the recovery process, a vacuum or pressure in the cavity 28, which was created based on deformation of the top wall 30, may act through the valve 18 to draw fluid and exudates from the wound site, to which the cover dressing is applied, into the cavity. Thus, the cavity, which is in line to flow of fluid from the wound site and also to the reservoir, may act as a passive pump that draws fluid from the wound site. Advantageously, the cavity of the apparatus 12 may maintain a vacuum therein between reset procedures, during which the top wall 30 is caused to become deformed or more deformed, in the absence of any action by or manipulation of the components of the apparatus 12.

Figure 3:
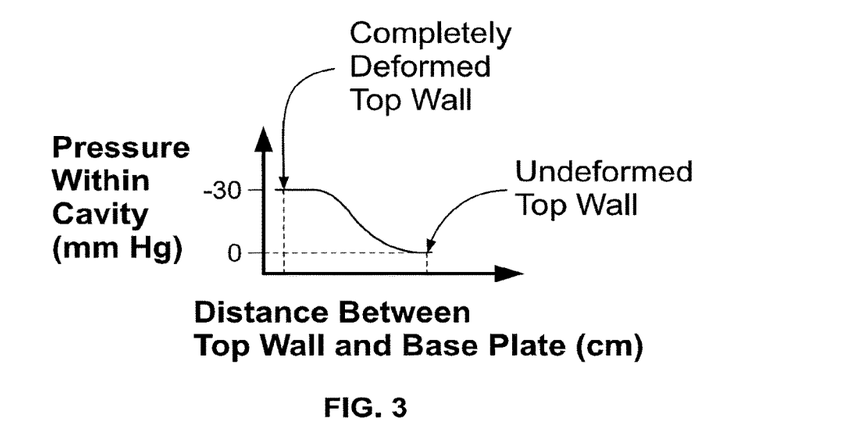
FIG. 3 is a graph illustrating a relationship between pressure and extent of deformation for the apparatus of FIG. 2.
Figure 16:
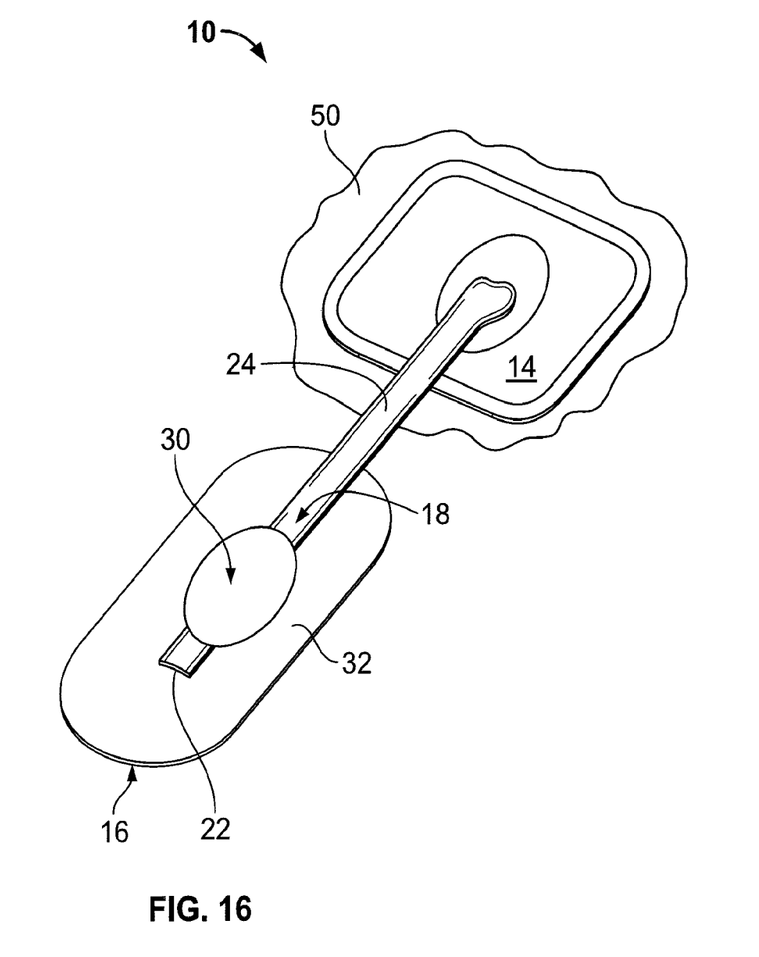
FIG. 16 is a schematic, plan view of a system for removing exudates from a wound site in an operative state, in accordance with an aspect of the invention.

Referring to FIG. 3, the deformation of the top wall 30 from its non-deformed state to a completely deformed state may result in a pressure within the cavity being changed from 0 to −80 mm Hg. In other words, a vacuum may be created internally within the cavity based on deformation of the top wall. Such vacuum may cause exudates to be drawn from the wound site into the cavity during a recovery process when the top wall is returning to its non-deformed state. FIG. 16 illustrates an exemplary implementation of the system 10 at a wound site 50 for drawing fluid from the wound site 50 into the reservoir 16.

In one embodiment, the cavity 28 may have a diameter of about 50 mm, and be adapted such that the top wall is spaced from the bottom plate about 5 mm and 10 mm when, respectively, 10 ml and 20 ml of exudate is contained within the cavity. In one embodiment, the cavity may have a one inch diameter and be operable to maintain a vacuum at −80 mm Hg.

Figure 4:
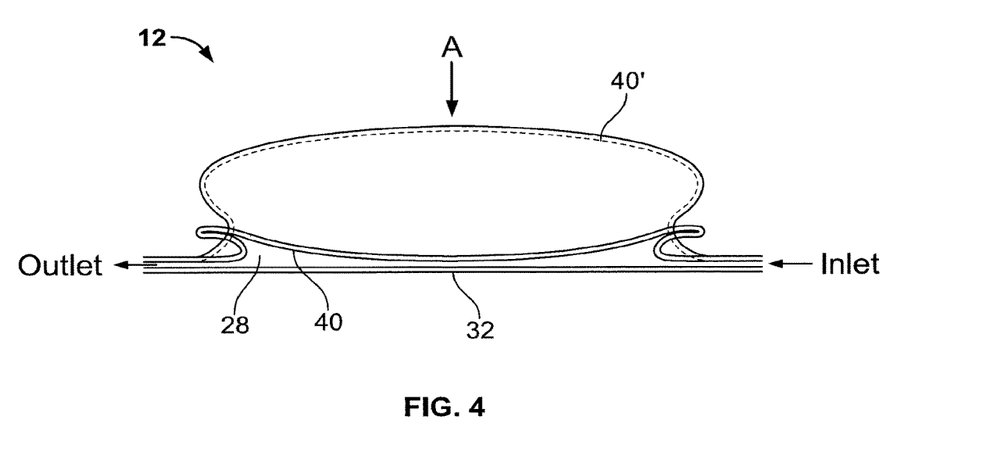
FIG. 4 is a schematic, cross-sectional view of an apparatus for controlling flow of fluid from a wound site, in accordance with an aspect of the invention.

Referring to FIG. 4, in an alternative embodiment, the apparatus 12 may include a deformable top wall 40 adapted such that, when a force is applied to the top wall 40 in the direction A toward the base plate 32 when the top wall 40 is in its non-deformed state as indicated by dashed lines 40', substantially the entirety of the wall 40 opposing the base 32 may become deformed.

Figure 5:
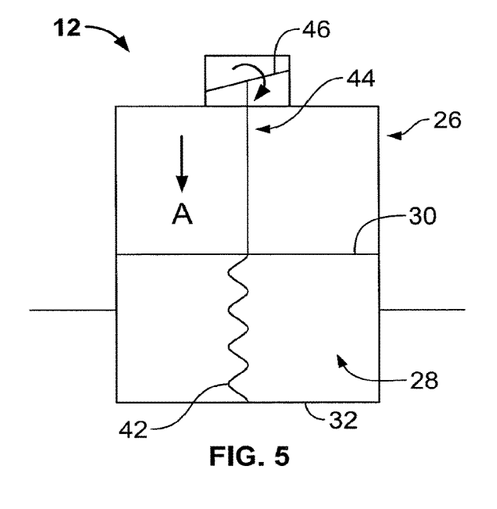
FIG. 5 is a schematic, cross-sectional view of an apparatus for controlling flow of fluid from a wound site, in accordance with an aspect of the invention.

Referring to FIG. 5, in another embodiment the apparatus 12 may include a spring element 42 extending between the top wall 30 and the base plate 32 that in combination form the cavity 28. The spring element 42 may serve as an additional support for the cavity 28, so as to maintain the cavity at a desired maximum volume state, which may be obtained when the top wall is in the non-deformed state. The pump element 26 may include a plunger device 44 that is mechanically operable, by application of a force on a handle 46 of the plunger device 44, to apply force in the direction A on the top wall 30, so as to deform the top wall 30 in the direction of the bottom plate 32, similarly as described above.

In one embodiment of the system 10, the conduits 24, the cavity portion of the apparatus 12 and the reservoir 16 may be combined into a single unit that is disposable with no air entrainment. For example, the system 10 may be supplied in an fully assembled state with the reservoir empty and the flexure pump chamber pre-collapsed, such that when the dressing 14 is applied to a wound site and the system 10 is activated, the pump chamber 28 expands to draw fluid from the wound site without first expelling air from the pump chamber into the reservoir 16.

In a further embodiment, the system 10 may be adapted to be air free, so as to decrease escape of odors from microleaks in joints and seals. Advantageously, the absence of air in the system 10 may improve efficiencies of the micropump, and also improve control of conduit barrier properties, in that air is more compressible than liquid and therefore more energy usually is expended to achieve a desired pressure in a system with air entrained than in one without.

In a further embodiment, the cavity 28 may include or be formed from absorptive filler material, similar to material used in the dressing applied to a wound site. The absorptive filler material of the cavity may include open cell foams, alginates, hydrofibers, CMC based materials and hydrocolloids. Desirably, the filler material can store fluids in a liquid form or absorb the wound fluid and form a gel to retain the exudate. In one embodiment in which the system 10 is used with the reservoir 16, the filler material may be a foam, which permits the fluid to be held as a fluid and then displaced into the reservoir when the pump chamber is compressed. In an embodiment in which the cavity 28 is of filler material that forms a gel, the system 10 may be used without the reservoir 16 and the non-return valve 22, such that the system 10 can be discarded when the pump chamber becomes full.

In one embodiment, the entire system, including the conduits, the passive pump apparatus including the cavity and pump element, valves and reservoir, may be made using a roll to roll process, such as with a tubular sheath at the outlet for attachment to a cover dressing. In one embodiment, all of the elements of the system may be made from relatively thin sheet materials which are unrolled, cut or perforated, and bonded together to form the different connected elements and then wound back onto a roll as a finished item, such that the system can be dispensed from the roll. Such system advantageously may have a very low cost construction, and minimizes packaging materials.

Figure 6:
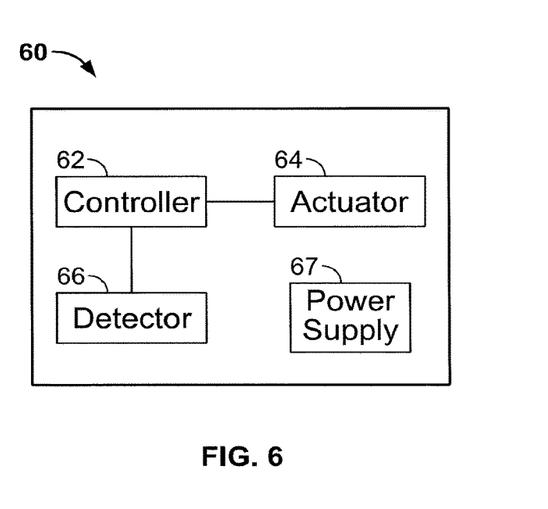
FIG. 6 is a block diagram of a fluid flow control device for use in an apparatus for controlling flow of fluid from a wound site, in accordance with an aspect of the invention.

In another embodiment, referring to FIG. 6, the apparatus 12 may be adapted to include an active element 60 operable to create or re-establish a vacuum within the cavity 28 of the apparatus 12. The active element desirably is arranged external to the cavity, so as to be isolated from fluids and exudates being held within and conveyed to and from the cavity, and thus prevent biofouling of the components of the active element. The active element 60 may include a controller 62 electrically coupled to an actuator device 64 and a proximity detector 66.

The proximity detector 66 may be a sensor, such as an infrared (IR) detector, that detects distance between the detector and an opposing object, such as the top wall 30. The detector 66 may provide detection information representative of the detected distance to the controller 62.

The controller 62 may include a processor and a memory including instructions executable by the processor to control actuation of the actuator device 64 based on detection information from the proximity detector 66. The instructions in the memory may also provide for active control of pressure within the cavity, by controlling operation of the actuator device 64. In addition, the active element may include a power supply 67, such as a battery, for providing electrical power to the components within the active element.

Figure 7:
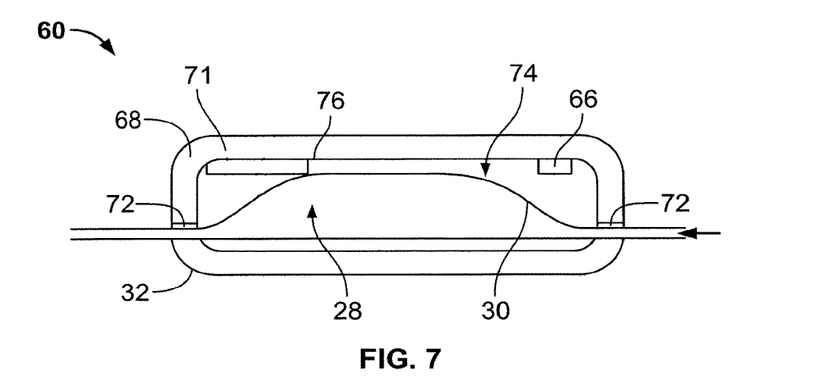
FIG. 7 is a schematic, cross-sectional view of an apparatus for controlling flow of fluid from a wound site, in accordance with an aspect of the invention.

Referring to FIG. 7, the active element 60 may be a part of or integrated with an outer wall 68 attached by seals 72 to the back plate 32. The outer wall 68 and the back plate 32, in combination, may define a sealed chamber 74 which is in fluid communication with the top wall 30 of the cavity 28. In one embodiment, the actuator device 64 may be an electronic micropump 71 attached to an interior surface 76 of the outer wall 68 and having an outlet (not shown) in fluid communication with the chamber 74. The pump 71 may be a miniature air pump or a reciprocating pump, or desirably a very compact low weight, low energy pump based on active material actuation technology, such as including a piezo ceramic material.

The controller 62 may operate the micropump 71 to create a desired pressure, such as positive pressure or a vacuum, within the chamber 74. The creation of a positive pressure within the chamber 74, in turn, may cause the top wall 30 to deform and, thus, compress the cavity 28 to create a vacuum within the cavity 28. Alternatively, the creation of a vacuum within the chamber 74 may cause or allow the top wall to become less deformed or return to its non-deformed state.

In one embodiment, after the top wall transitions to a less deformed or its non-deformed state, such as may occur when a leak is formed at the dressing attachment to the wound site, the controller may cause the pump 71 to create a positive pressure in the chamber 74 tore-start withdrawal of exudate from a wound site, after the leak that formed at the dressing attachment to the wound site has been sealed.

In an exemplary operation of the apparatus 12, the active element 60 may control the micropump 71 to maintain or change pressure within the chamber 74 to ensure that either continuous or intermittent vacuums are applied to the wound site, while a primary vacuum is sustained at the wound site based on the configuration of the cavity. The primary vacuum is a function of the extent that the top wall is or has been deformed. The cavity, thus, may serve as a passive pump that can be acted upon by the active element 60, such as based on controlled operation of the micropump 71, so that a vacuum is continuously or intermittently applied to the wound site. Advantageously, the active element 60 may operate to reset or re-prime the passive pump during a reset process, in other words, to re-establish a desired pressure within the cavity 28, by suitably creating a positive pressure in the chamber 74. The reset process functionality of the active element may permit the apparatus 12 to continue to operate even if a leak is developed at the wound site, which may cause a vacuum within the cavity, which is in fluid communication with the wound site, to be at least partially lost.

In one embodiment, during a process to reset the passive pump, exudates collected within the cavity may be forced from the cavity, through the valve 22 and into the reservoir 16, and the vacuum within the cavity 28 may be re-established by creating a positive pressure within the chamber 74.

The valves 18 and 22 may provide for a desired direction of fluid flow in the system 10, such as movement of fluid from the wound site, through the apparatus 12 including a pumping means, to the reservoir, and avoid fluid from being pushed back to the wound site when resetting the actuator device. In one embodiment, the size and configuration of the chamber 74 and the cavity 28, and the capacity of the pump 71, may be designed to optimize the reset process. In one embodiment, the cavity and the reservoir may be independently optimized. For example, the reservoir may have a low profile and become filled to accommodate only the amount of exudate liberated from the wound. In one embodiment, the reservoir may be arranged so that a sum of the volume of the reservoir and volume of fluid in the reservoir is less than 25%, less than 15% or less than 10% greater than the volume of the fluid.

In a further embodiment, the detector 66 may be attached to the interior surface 76 of the outer wall 68 to oppose a portion of the top wall 28 that may become deformed. The controller 62 may, based on detection information provided by the detector 66 indicating the distance between the opposing portion of the top wall and the detector, determine when the cavity is full or nearly full of exudate, and also monitor the rate at which the cavity 28 fills with exudate. Depending on a determination of the extent the cavity is filled with exudate, the controller may control the pump 71 to generate positive pressure within the chamber 74, to cause the contents of the cavity to empty into the reservoir 16 and create a vacuum within the cavity, which can result in additional exudate to be drawn from the wound site to the cavity.

In another embodiment, the controller 62 may use detection information obtained from the detector 66 to assess exudate evolution rates and detect leaks at the dressing 14. Also, the controller 62 may provide for a controlled rate of return of exudates to optimize vacuum pressure levels in the passive pump cavity.

Advantageously, the evolution rates and leak detection may be determined by a device, in particular, the active element 60, which is maintained isolated from fluids and exudate drawn from the wound site, and which also may be a separate and re-usable part of the system. The isolation of the active element may provide for reduced cost in terms of disposable and non-disposable elements of the system.

In one embodiment, in an apparatus adapted to have low energy consumption, the active element 60 may utilize less rigorous seals 72, or no seals may be needed on the active element, due to the ease with which pressure within the cavity may be reset using the micropump. In such embodiment, although more energy is used to reset pressure, a higher cost associated with manufacture of the apparatus with seals that make the apparatus relatively leak free, and difficulties with reliably manufacturing a leak free apparatus, may be avoided.

Also, the system of the invention may be made sufficiently small and portable, and also sized according to patient need, independent of the size of the micropump.

In a further embodiment, referring to FIGS. 5 and 6, an active element 60 may be included in the apparatus 12, and the actuator device 64 may be a solenoid operable by the controller to force the plunger 44 in the direction A to deform the top wall 30 and thus create a vacuum in the cavity 28.

Figure 8:
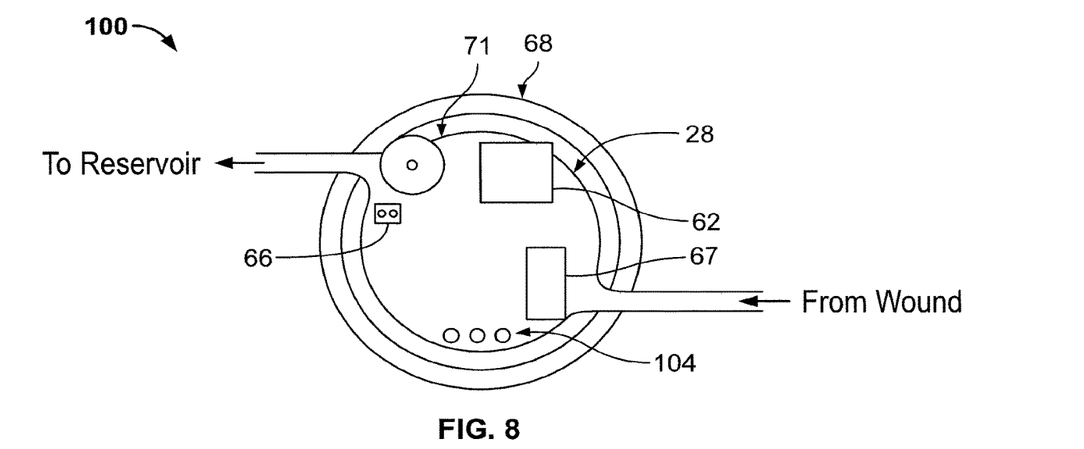
FIG. 8 is a schematic, plan view of an apparatus for controlling flow of fluid from a wound site, in accordance with an aspect of the invention.
Figure 9:
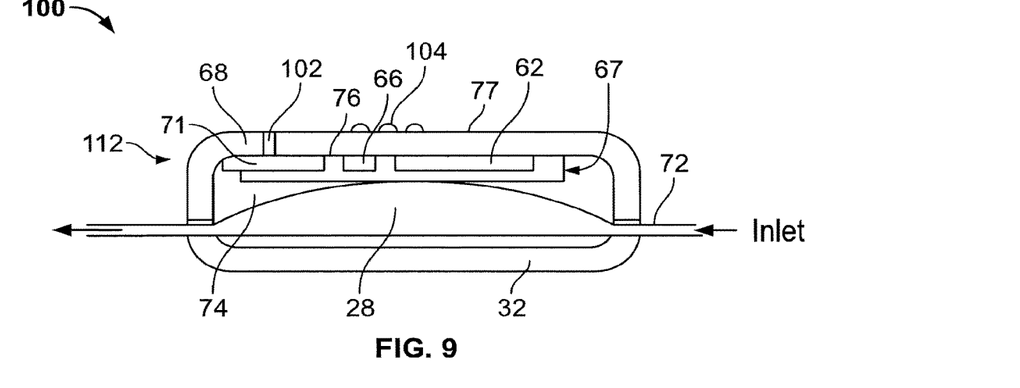
FIG. 9 is a schematic, cross-sectional view of the apparatus of FIG. 8.

In one embodiment, referring to FIGS. 8 and 9, a system for removing exudates from a wound site 100 may contain a flow control apparatus 112 including components that are the same or substantially similar to those of the apparatus 12 of the system 10 described above. Like reference numerals are used to describe the same components in the system 10 contained in the system 100. Referring to FIGS. 8 and 9, the apparatus 112 may include a micropump 71, a controller 62, a proximity detector 66 and a battery 67 attached to the interior surface 76 of the outer wall 68 of the apparatus 112. The apparatus 112 further may include a vent 102 extending through the thickness of the outer wall 68 to an outlet port (not shown) of the micropump 71. In addition, the apparatus 112 may include indicators 104, such as LEDs, attached to an outer surface 77 of the outer wall 68 and electrically connected to the controller 62. The controller 62, based on detection information provided by the detector 66, may cause the LEDs 104 to illuminate, for example, based on a determined evolution rate or a determination that the outer wall is not transitioning between a deformed and non-deformed state, as may occur if the pump 71 malfunctions or ceases to function.

In one embodiment, the controller 62 may operate to provide that mismatches between the stroke capacities of the active element, such as the micropump, and mechanical impedance to fluid flow in system components are overcome, thereby providing higher pumping efficiency.

Also, the controller 62 may operate the pump so as to optimize electrical power utilization of the battery.

In addition, the controller 62 may cause one or more of the indicators 104 to illuminate when the controller 62 determines a low battery level.

Figure 10:
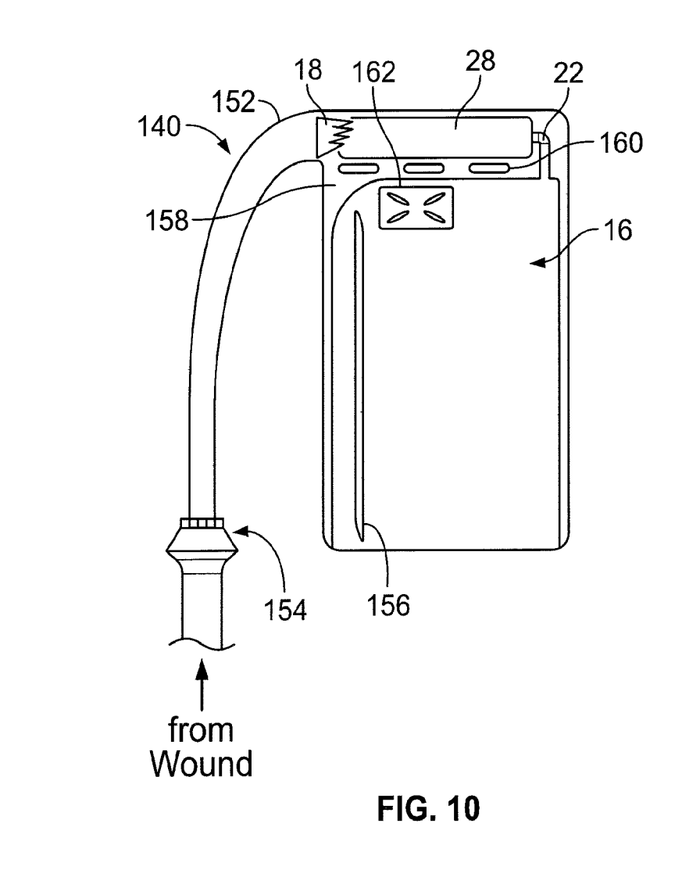
FIG. 10 is a schematic view of a system for removing exudates from a wound site, in accordance with an aspect of the invention.

In one embodiment, a system for removing exudates from a wound site 140 having the same or similar components and functionality as components of the system 10 may be adapted for mounting to an object or a patient, as illustrated in FIG. 10. Like reference numerals are used to describe like components of the system 10, as previously described. Referring to FIG. 10, the system 140 may be an integrated device including the components of the apparatus 12 and the reservoir 16. The cavity is in fluid communication with the reservoir 16 through a valve 22, and a valve 18 interconnects the cavity with a conduit 152 having an end terminated with a leak proof connector 154, which is for connection to a connector (not shown) of a dressing. The apparatus 12 may further include a reservoir level indicator 156 disposed on an outer surface of the reservoir 16 to indicate the extent to which the reservoir is filled with exudate. The level indicator 156 may be in the form of a clear window through which the interior of the reservoir may be viewed, or alternatively may be a color changing strip, such as litmus paper that changes color on contact with the fluid, or a moisture sensitive material. In addition, the apparatus 12 may include a strip 158 of material, such as pressure sensitive adhesive, silicone adhesive, hydrocolloid or hook and loop, attaching the reservoir to the cavity 28, and to which mounting clips are attached to allow the apparatus 12 to be secured to an object. Further, the system 140 may include a gas filter 162, such as a charcoal filter, adapted in relation to the reservoir so as to be bonded or glued to cover a window cut through the wall of the reservoir. In addition, the filter may have olephobic and hydrophobic properties to allow the release of gas without allowing fluids to pass through and potentially leak.

Figure 11:
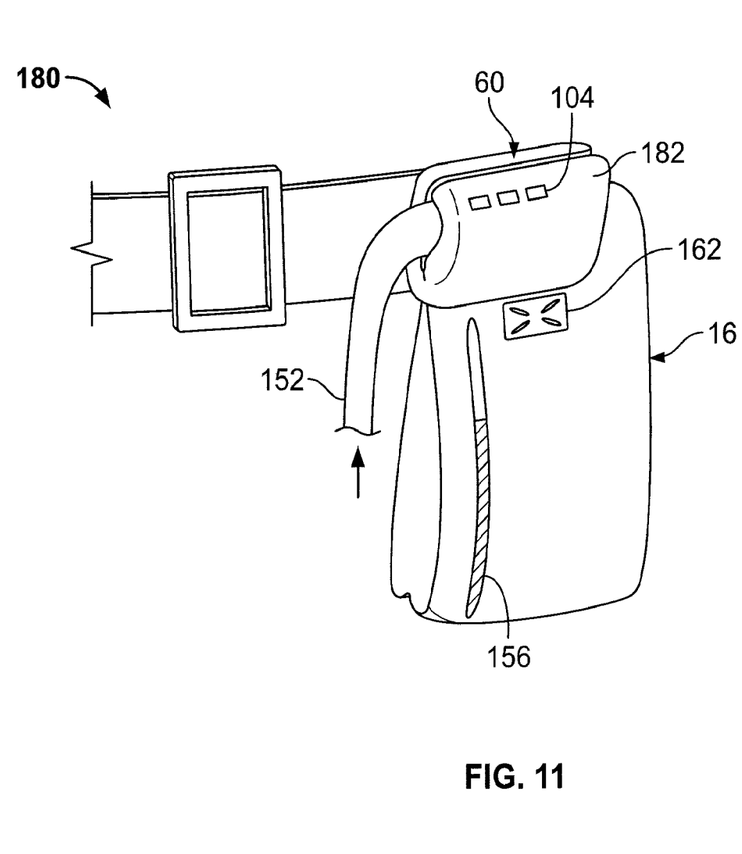
FIG. 11 is a schematic view of a system for removing exudates from a wound site, in accordance with another aspect of the invention.

In another embodiment, a system for removing exudates from a wound site 180 having the same or similar components and functionality as components of the system 100 may be adapted for mounting to a belt of a patient, such as shown in FIG. 11. Like reference numerals are used to describe like components of the system 100, as previously described. Referring to FIG. 11, the system 180 may be an integrated device including the reservoir 16 having a bag-shaped configuration, and a housing 182 containing the components of the apparatus 12 and the active element 60 and connected to the reservoir 16. The system 180 further may include LEDs 104 on an outer surface of the housing 182, a conduit 152 to be connected in fluid communication with a wound site, a reservoir fill level indicator 156 and a reservoir filter 162.

Figure 12:
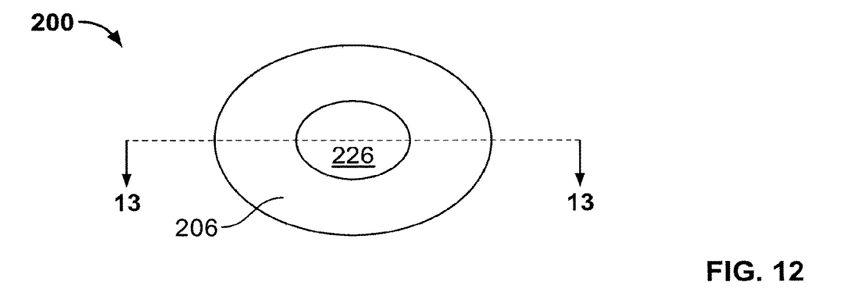
FIG. 12 is a top plan view of an apparatus for controlling flow of fluid, in accordance with aspect of the invention.
Figure 13:
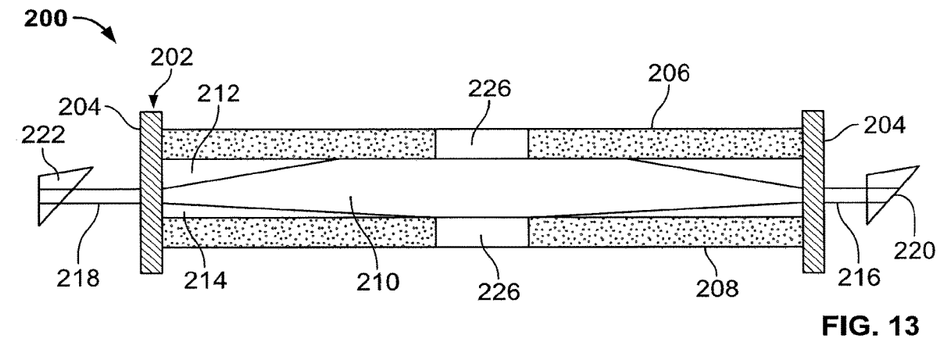
FIG. 13 is a cross-sectional view of the apparatus of FIG. 12 at line 13-13.
Figure 14:
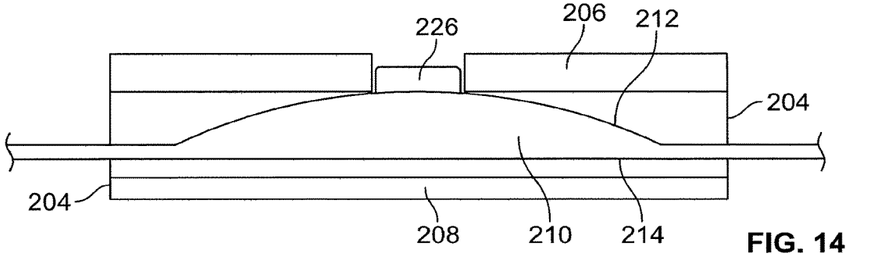
FIG. 14 is a cross-sectional view of another embodiment of an apparatus for controlling flow of fluid, in accordance with an aspect of the invention.

In another aspect, the actuator device of the apparatus of the disclosure may be a piezoelectric device arranged to act on a wall defining the self-filling cavity, so as to deform the wall and, thus, compress the cavity to decrease the volumetric capacity of the cavity and, hence, create a desired pressure or vacuum in the cavity. Referring to FIGS. 12-13, a flow control apparatus 200 may include a housing 202 having end walls 204 to which a top plate 206 and a base plate 208 are connected. The housing 202 encloses a self-filling cavity 210 defined by a top wall 212 and bottom wall 214 which connect the cavity, at an inlet port 216 and an outlet port 218, in fluid communication with respective input and outlet valves 220, 222 which are for connection to an exudate reservoir (not shown) and a dressing (not shown) to be applied at a wound site. The top plate 206 and the bottom plate 208 may include a piezoelectric device 226 disposed in relation to the top and bottom walls 212, 214, respectively, so that the top and bottom walls may be deformed when one or both of the piezoelectric devices 226 is actuated. When the device 226 is actuated, the wall opposing the device 226 is compressed, to create a vacuum in the cavity, while the housing end walls 204 maintain the actuator edges fixed during movement. As the edges are fixed during movement, the volume in the chamber is forced to be reduced when the actuators move inwards, and thus a vacuum is created to draw off the wound fluid when the actuators move outwardly to a non-actuated position.

In one exemplary embodiment, the apparatus 200 may provide that the piezoelectric device 226 is operated to vibrate at up to 1.8 KHz and cause movement of the wall of the cavity opposing the device 226 away from the device 226 a distance of about 25 microns.

In another exemplary operation of the apparatus 200, the piezoelectric devices may be used to drive a fluid coupled "reset," such as by being actuated over several cycles, similarly as described above with reference to FIG. 7 regarding actuation of a micropump using a secondary fluid to interact with a first fluid. Referring to FIG. 7, the micropump 71 evacuates the first fluid out of the cavity 74 to reset the actuator and allow a vacuum to be applied to draw fluid from the wound site into cavity 28. Although a piezo micropump may only move short distances with each cycle, for example, 47 micrometers, it can operate at a high cycle rate, such as 1.8 KHz. For each cycle, the very small movement may draw a very small amount of fluid from the chamber and push the fluid out through the hole. The spring or other bias effectively resets the chamber's position after each cycle, so that the chamber is ready for the next cycle. Advantageously, the piezo drive micropump may be very small, such as about 1 inch in diameter, and use little energy, and by operating over several cycles, a sufficient amount of fluid may be moved to create, for example, an 80 mm Hg vacuum.

In another embodiment, the base plate 208 of the apparatus 200 may include resilient material to provide a bias against the bottom wall 214 that defines the cavity 210.

Figure 15:
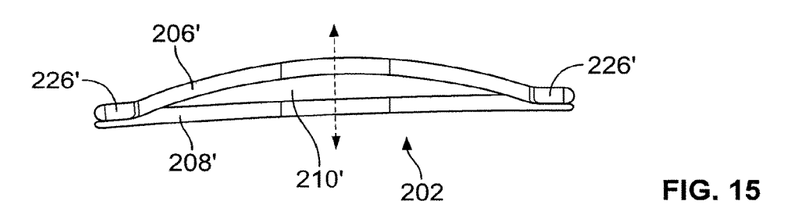
FIG. 15 is a cross-sectional view of another embodiment of an apparatus for controlling flow of fluid, in accordance with an aspect of the invention.

In another embodiment, referring to FIG. 15, the housing 202 of the apparatus 200 may include a top plate 206' and base plate 208', and piezoelectric devices 226' that interconnect the base and top plates at, or form a circumferential edge or ring, of a cavity 210'. In an exemplary operation of this embodiment, when the devices 226' are cycled between an actuated state and a non-actuated state, the circumference becomes shorter or longer causing the top and bottom plates to move outwards or inwards and, hence, the volume in the cavity increases or decreases.

Figure 17:
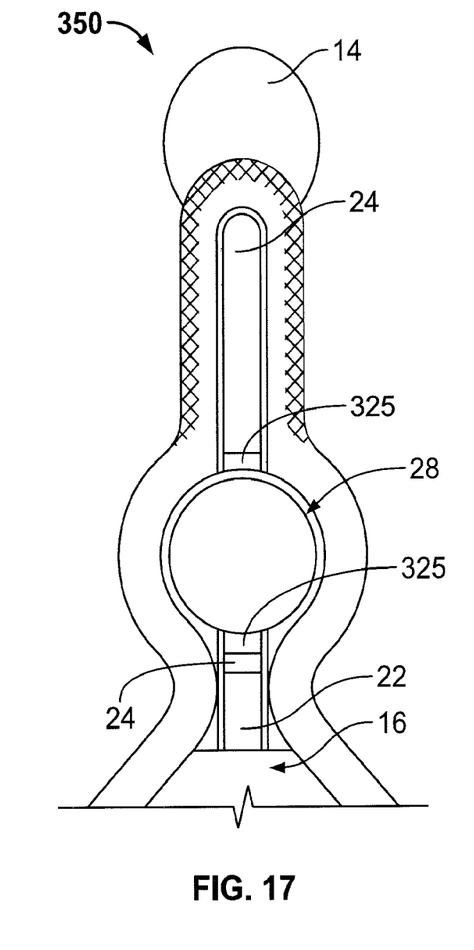
FIG. 17 is a schematic, plan view of an exemplary a system foremoving exudates from a wound site, in accordance with an aspect of the invention.

FIG. 17 illustrates an exemplary system for drawing fluid from a wound site 350 that may include the same or similar components as in the system 10. Referring to FIG. 18, the system 350 may further include a pinch valve 325 at the inlet and outlet of the cavity 28 to control flow of fluid into and out of the cavity 28.

Overall, the invention advantageously may provide therapy by way of a minimally sized, airless and disposable system. The reservoir desirably may be reduced in size in relation to the expected amount of fluid to be drawn from a wound site. In addition, disposable and reusable components may be combined in a cost effective manner and to make the system practical for use in a home setting. Further, the system may be adapted to address inefficiency by controlling the amount of air moved during treatment, as suitable. Also, the system may be made environmentally sound.

Although the invention herein has been described with reference to particular embodiments, it is to be understood that these embodiments are merely illustrative of the principles and applications of the present invention. The following numbered paragraphs additionally describe embodiments of the invention as set forth herein.

The invention claimed is:

1. A vacuum wound therapy apparatus comprising:
a sealed chamber including a first wall, a second wall, a first seal, and a second seal, wherein the first wall and the second wall define the sealed chamber;
a cavity disposed within the sealed chamber, the cavity configured for fluid communication with a wound site and with a reservoir that receives and holds wound exudate, the cavity including an input for communication with the wound site, wherein the first seal is located at the input, an output for communication with the reservoir, wherein the second seal is located at the output, and a first non-rigid, deformable wall in fluid communication with the sealed chamber, the first non-rigid, deformable wall opposing at least one of the first wall and the second wall; the cavity having a first state being deformed and a second state being non-deformed or less deformed than the first state, wherein the cavity is adapted to draw exudate from the wound site into the cavity and to manage exudate flow between the wound site and the reservoir during transition of the cavity between the first state and the second state;
a piezoelectric device located at the first wall and in fluid communication with the sealed chamber, wherein the piezoelectric device is adapted to deform the first non-rigid deformable wall of the cavity in the direction of the second wall to transition the cavity from the second state to the first state, wherein the piezoelectric device provides a pressure within the sealed chamber to cause the first non-rigid deformable wall to be deformed in the first state and to compress the cavity.

2. The vacuum wound therapy apparatus of claim 1 further comprising the reservoir.

3. The vacuum wound therapy apparatus of claim 2 further comprising a housing wherein the sealed chamber, the cavity, the piezoelectric device, and the reservoir are contained by the housing to form an integrated vacuum wound therapy device.

4. The vacuum wound therapy apparatus of claim 1, wherein the cavity is adapted to push exudate into the reservoir when the cavity is transitioning from the second state to the first state.

5. The vacuum wound therapy apparatus of claim 4, wherein the cavity is adapted to draw exudate from the wound site into the cavity when the cavity is transitioning from the first state to the second state.

6. The vacuum wound therapy apparatus of claim 5 further comprising a spring element associated with the cavity to maintain the cavity at a desired maximum volume state when the piezoelectric device is in the non-actuated state.

7. The vacuum wound therapy apparatus of claim 5 wherein the piezoelectric device is actuated between an actuated state and a non-actuated state to deform the first non-rigid, deformable wall in the actuated state and to release the first non-rigid, deformable wall in the non-actuated state.

8. The vacuum wound therapy apparatus of claim 7 wherein the piezoelectric device is operated between the actuated state and the non-actuated state at a pre-determined cycle rate to push fluid to the reservoir during each actuated state.

9. The vacuum wound therapy apparatus of claim 8 wherein the predetermined cycle rate is about 1.8 KHz.

10. The vacuum wound therapy apparatus of claim 8 further comprising a second piezoelectric device, wherein the cavity includes a second non-rigid, deformable wall and the second piezoelectric device is located adjacently to the second non-rigid deformable wall, wherein one of or both of the first and second non-rigid, deformable walls are deformed when one of or both of the first and second piezoelectric devices are actuated.

11. A vacuum wound therapy apparatus comprising:
an active element including a wall defining a sealed chamber and a pump attached to an interior surface of the wall, the pump having an outlet in fluid communication with the sealed chamber, wherein the sealed chamber includes a first seal and a second seal;
a cavity disposed within the sealed chamber, the cavity including an input at the first seal, the input for communication with a wound site, an output at the second seal, the output for communication with a reservoir, and a non-rigid, deformable wall in fluid communication with the sealed chamber; and
a controller operatively connected to the pump, including a processor and a memory, configured to store instructions, wherein the processor is configured to execute the stored instructions to:
actuate the pump to apply a fluid pressure within the sealed chamber to transition the cavity from an expanded state to a compressed state to force exudate from the cavity to a reservoir.

12. The vacuum wound therapy apparatus of claim 11 wherein the processor is configured to execute the stored instructions to:

release the fluid pressure within the sealed chamber to transition the cavity from the compressed state to an expanded state to remove exudate from the wound site.

13. The vacuum wound therapy apparatus of claim 12 wherein the processor is configured to execute stored instruction to:
release the fluid pressure within the sealed chamber by actuating the pump to reduce the fluid pressure within the sealed chamber.

14. The vacuum wound therapy apparatus of claim 13 wherein the pump comprises a piezoelectric device and the processor is configured to execute stored instructions to:
actuate the piezoelectric device between an actuated state and a non-actuated state to deform the non-rigid, deformable wall in the actuated state and to release the non-rigid, deformable wall in the non-actuated state.

15. The vacuum wound therapy device of claim 14 wherein the processor is configured to execute stored instructions to:
actuate the piezoelectric device between the actuated state and the non-actuated state at a pre-determined cycle rate to push fluid to the reservoir during each actuated state.

16. The vacuum wound therapy device of claim 12 further comprising a detector operatively connected to the controller, wherein the detector determines a distance between the non-rigid deformable wall and the detector.

17. The vacuum wound therapy device of claim 16 wherein the processor is configured to execute stored program instructions to:
actuate the pump based on the distance determined by the detector.

18. The vacuum wound therapy device of claim 17 wherein the processor is configured to execute stored program instructions to:
actuate the pump to control the rate of return of the exudates being removed from the wound site.

19. The vacuum wound therapy apparatus of claim 18 wherein the processor is configured to execute stored program instructions to:
actuate the pump to assess exudate evolution rates.

20. The vacuum wound therapy apparatus of claim 19 wherein the processor is configured to execute stored program instructions to:
detect a leak occurring at the wound site.

* * * * *